(12) United States Patent
Campbell et al.

(10) Patent No.: US 8,800,712 B2
(45) Date of Patent: Aug. 12, 2014

(54) EAR TIP PIECE FOR ATTENUATING SOUND

(75) Inventors: Don E. K. Campbell, Longwood, FL (US); William Chiu, Longwood, FL (US)

(73) Assignee: Magnatone Hearing Aid Corporation, Casselberry, FL (US)

( * ) Notice: Subject to any disclaimer, the term of this patent is extended or adjusted under 35 U.S.C. 154(b) by 0 days.

(21) Appl. No.: 13/593,205

(22) Filed: Aug. 23, 2012

(65) Prior Publication Data

US 2013/0056295 A1 Mar. 7, 2013

Related U.S. Application Data

(63) Continuation-in-part of application No. 13/199,309, filed on Aug. 25, 2011.

(51) Int. Cl.
*A61B 7/02* (2006.01)

(52) U.S. Cl.
USPC .......................................................... 181/135

(58) Field of Classification Search
USPC .......................................................... 181/135
See application file for complete search history.

(56) References Cited

U.S. PATENT DOCUMENTS

| 3,050,056 | A | | 8/1962 | Dressler |
|---|---|---|---|---|
| 3,602,330 | A | * | 8/1971 | Johnson ........................ 181/135 |
| 3,934,100 | A | | 1/1976 | Harada |
| 4,338,929 | A | | 7/1982 | Lundin et al. |
| D267,429 | S | | 12/1982 | Harada |
| 4,540,063 | A | * | 9/1985 | Ochi et al. ..................... 181/135 |
| 4,880,076 | A | | 11/1989 | Ahlberg et al. |
| 4,972,488 | A | | 11/1990 | Weiss et al. |
| 5,247,946 | A | | 9/1993 | Holder |
| 5,333,622 | A | | 8/1994 | Casali et al. |
| 5,824,968 | A | | 10/1998 | Packard et al. |
| 5,936,208 | A | * | 8/1999 | Hamery ........................ 181/135 |
| 5,987,146 | A | | 11/1999 | Pluvinage et al. |
| 6,000,492 | A | | 12/1999 | Puthuff et al. |
| D419,675 | S | | 1/2000 | Garcia |
| D420,136 | S | | 2/2000 | Barnard et al. |
| D431,294 | S | | 9/2000 | Barnard et al. |
| 6,129,175 | A | | 10/2000 | Tutor et al. |
| 6,179,085 | B1 | | 1/2001 | Brimhall et al. |
| 6,275,596 | B1 | | 8/2001 | Fretz et al. |
| 6,359,993 | B2 | | 3/2002 | Brimhall |
| 6,513,621 | B1 | | 2/2003 | Deslauriers et al. |
| 6,532,295 | B1 | | 3/2003 | Brimhall et al. |
| 6,577,740 | B1 | | 6/2003 | Bordewijk |
| 6,801,629 | B2 | | 10/2004 | Brimhall et al. |
| D518,179 | S | | 3/2006 | Holmes |
| 7,013,016 | B2 | | 3/2006 | Wolf |

(Continued)

OTHER PUBLICATIONS

Keidser, Gitte et al., "Relative Loudness Perception of Low and High Frequency Sounds in the Open and Occluded Ear," J. Accoust. Soc. Am., Jun. 2000, 3351-7, vol. 107(6), USA.

(Continued)

*Primary Examiner* — Forrest M Phillips
(74) *Attorney, Agent, or Firm* — Ice Miller LLP (57) ABSTRACT

An ear tip piece device made of resilient material dimensioned for fitting the ear canal of a wearer, having a solid portion, a reversibly compressible portion, a channel and a sound attenuating element positioned inside the channel for attenuating sound being transmitted to the ear. In one embodiment, the ear tip piece is asymmetrical due to a bend.

22 Claims, 9 Drawing Sheets

(56) References Cited

U.S. PATENT DOCUMENTS

| | | | |
|---|---|---|---|
| 7,027,608 | B2 | 4/2006 | Fretz et al. |
| 7,065,223 | B2 | 6/2006 | Westerkull |
| 7,110,562 | B1 | 9/2006 | Feeley et al. |
| 7,130,437 | B2 | 10/2006 | Stonikas et al. |
| 7,240,765 | B2 | 7/2007 | Berg et al. |
| 7,313,245 | B1 | 12/2007 | Shennib |
| 7,418,105 | B2 | 8/2008 | McIntosh |
| 7,537,011 | B2 | 5/2009 | Falco |
| 7,602,933 | B2 | 10/2009 | Cartwright et al. |
| 7,864,972 | B2 | 1/2011 | McIntosh et al. |
| 7,889,883 | B2 | 2/2011 | Cartwright et al. |
| 7,899,200 | B2 | 3/2011 | Karamuk et al. |
| 7,940,946 | B2 | 5/2011 | Caldarola |
| 8,083,022 | B2 * | 12/2011 | Gommel et al. ............ 181/135 |
| 2002/0179365 | A1 * | 12/2002 | Meussen et al. ............ 181/135 |
| 2005/0147267 | A1 | 7/2005 | Gudmundsen et al. |
| 2005/0190939 | A1 | 9/2005 | Fretz |
| 2006/0147071 | A1 * | 7/2006 | Neilson ................... 381/325 |
| 2006/0171549 | A1 | 8/2006 | Holmes |
| 2006/0256990 | A1 | 11/2006 | Holmes |
| 2008/0276945 | A1 | 11/2008 | Rosen |
| 2009/0067661 | A1 | 3/2009 | Keady et al. |
| 2010/0084217 | A1 | 4/2010 | Blanchard |
| 2010/0307859 | A1 * | 12/2010 | Lopez et al. ............... 181/129 |
| 2011/0051979 | A1 * | 3/2011 | Lee et al. .................. 381/380 |
| 2011/0103605 | A1 * | 5/2011 | Killion et al. ............... 381/72 |
| 2011/0223864 | A1 * | 9/2011 | Wai ........................ 455/41.3 |

OTHER PUBLICATIONS

Niquette, Patricia A., "Occupational Hearing Conservation—Uniform Attenuation Hearing Protection Devices," Hearing Review, Mar. 2007, USA.

Letowski, T. et al., "Speech Communication with Flat-Attenuation Hearing Protectors," Internoise, Nov. 16-18, 1998, Christchurch, New Zealand.

Killion, Mead et al., "An Earplug with Uniform 15-dB Attenuation," The Hearing Journal, May 1988, p. 14-17, vol. 41 (5), USA.

Mueller, H. Gustav et al., Augiologists' Desk Reference, Mar. 1, 1998, p. 288-9, 360-1, vol. II, Singular Publishing Group, Inc., San Diego, CA, USA.

Killion, Mead C., The Parvum Bonum, Plus Melius Fallacy in Earplug Selection, 1993, p. 426-431, Scanticon, Kolding, Denmark.

Sandlin, Robert E., Hearing Instrument Science & Fitting Practices, Second Edition, 1996, p. 556, National Institute for Hearing Instruments Studies, USA.

Berger, Elliott H., "A New Hearing Protection Attenuation Standard—ANSI S12.6," EARLOG16, 1985, Aearo Company, Indianapolis, IN, USA.

International Search Report and Written Opinion for PCT/US12/00371, Nov. 19, 2012.

International Search Report and Written Opinion for PCT/US12/00370, Dec. 24, 2012.

* cited by examiner

— EAR TIP PIECE FOR ATTENUATING SOUND —

This is a continuation-in-part application of application Ser. No. 13/199,309, filed Aug. 25, 2011, which is hereby incorporated by reference in its entirety.

FIELD OF THE INVENTION

The present invention is directed to an ear tip piece comprising a solid portion and a reversibly compressible portion designed to conform to a person's ear canal and to be used in conjunction with hearing instruments, such as earphones, ear plugs, personal sound amplifiers, or the like.

BACKGROUND OF THE INVENTION

A semi-customized ear tip piece for insertion in an ear canal is disclosed that has a first end and a second end, wherein the first end includes a solid portion and the second end includes a reversibly compressible portion. A first channel is disclosed that passes through the solid portion for transmitting sound to the ear. In a preferred embodiment, the ear tip piece also has a bend. In an alternative embodiment, the solid portion comprises a base and a projection. The disclosed ear tip piece is preferably used in conjunction with various hearing instruments, such as Behind-the-ear ("BTE"), Over-the-ear ("OTE"), Receiver-in-canal ("RIC"), or Receiver and Microphone in canal hearing aids.

BTE or OTE hearing aids typically use an ear tip piece to locate and direct the amplified sound into the wearer's ear canal. RIC hearing aids use an ear tip piece as a holder to position the receiver or transducer in the ear canal. The majority of the ear tips currently on the market are of a symmetrical circular or oval shape with a round or dome shaped tip. It is important for acoustic reasons and for wearer comfort, to have the tip fit well.

Such known ear tip pieces are disclosed in U.S. Pat. No. 7,889,883 and U.S. Pat. No. 7,602,933, both issued to Cartwright et al. The ear tip pieces disclosed in the '883 and '933 patents have a generally cone-shaped appearance (or otherwise referred to as a "bullet-shape") and at the conical end, a central longitudinal passage is provided which can further be associated with various tube-like structures. The '883 and '933 patent ear tip pieces are comprised of material that is preferably a highly flexible and/or pliable material that can be compressed in a fashion so that distinct folds are formed in the material, creating what appears to be a "star-like" configuration when fully compressed along each fold line. The fold lines themselves can be depressions in the flexible material itself, physically scored into the material, or otherwise provided.

U.S. Pat. No. 7,027,608 issued to Fretz et al. discloses several embodiments of eartips. The '608 patent discloses a bud-shaped eartip that is a conically shaped member having a through bore for sound transmission and an interior socket configured to allow the bud-shaped eartip to be received on the honey dipper end of a tube. A flower-shaped eartip is disclosed that includes a central core and three flower petals extending from the central core. Each of the petals has a substantially ellipsoidal shaped end. The '608 patent discloses a variation of the flower eartip, the webbed flower eartip, in which the flower petals are connected by a thin web of eartip material. The webbed flower eartip will reduce the ambient sounds passage through the ear canal increasing occlusion. Another eartip disclosed in the '608 patent is the guppie-shaped eartip which includes a central body portion and a tail. The '608 patent also discloses a barb-shaped eartip including a central body portion and a barb extending from the central body portion. Another variation of an eartip disclosed in the '608 patent is a dome-shaped eartip having a bud-shaped core and a skirt starting about half way down the bud-shape and extending from the core. Yet another eartip variation disclosed in the '608 patent is a bud-shaped eartip having a wax flap.

In another alternative embodiment, the ear tip piece has a sound attenuator inserted into the first channel to attenuate sound being transmitted to an ear. In a preferred embodiment, a coupler is inserted into the first channel and retains the sound attenuator. The disclosed ear tip piece is preferably used as an earplug to attenuate the loudness or decibel level of damaging frequencies of sound.

A human ear naturally resonates or amplifies the loudness of certain frequencies of sound to provide better hearing. The human ear's most sensitive region for hearing ranges from approximately 1000 Hertz ("Hz") to 4000 Hz, which encompasses the range of typical frequencies for spoken word. The ear naturally resonates this range of frequencies and provides peak resonances at approximately 2700 Hz and 4000 Hz. For instance, the natural resonance at 2700 Hz is about 18 decibels ("dB") of amplification and the natural resonance at 4000 Hz is about 9 dB for conversational levels. The ear does not generally resonate frequencies below 1000 Hz and provides very little resonance below 500 Hz.

Since frequencies between 1000 Hz and 4000 Hz have the highest natural resonance, they are also the most sensitive to increases in loudness and, as a result, are the most at risk for hearing loss. The reason these frequencies are most at risk for hearing loss is because loudness or sound pressure level discomfort is achieved at high levels for this range before lower or higher frequencies are affected.

A study by National Acoustic Laboratories, Australia in 1999 found that placing a typical earplug in a wearer's ear creates an "insertion effect". This "insertion effect" causes the wearer to desire an additional 7 dB of amplification or gain in low frequencies to maintain the same perception of those low frequencies as for 1000 Hz frequencies. As a result, a uniform attenuation of all frequencies, such as that generally provided by foam or custom earplugs, may detrimentally alter the quality of sound heard by a wearer.

SUMMARY OF THE INVENTION

An ear tip piece for insertion in an ear canal is disclosed that comprises a first end including a solid portion that is sized and shaped to be inserted into an ear canal, a second end including a reversibly compressible portion for sealing the ear canal, and a first channel passing through the solid portion for transmitting sound to the ear. In an alternative embodiment, the ear tip piece further comprises a bend between the first end and second end, wherein the bend is positioned to facilitate insertion of the ear tip piece at or near a first or second narrowing or bend of an ear canal when the first end is inserted into the ear canal. In a further alternative embodiment, the reversibly compressible portion is hollow. In another alternative embodiment, the solid portion comprises a base and a projection extending from the base, the first channel passing through the projection.

In an alternative embodiment, an ear tip piece for insertion in an ear canal is disclosed that comprises a first end including a solid portion that is sized and shaped to be inserted into an ear canal and a second end including a reversibly compressible portion for sealing the ear canal. The ear tip piece further comprises a bend between the first end and the second end, wherein the bend is positioned to facilitate insertion of the ear tip piece at or near a first or second narrowing or bend of an ear canal when the first end is inserted into the ear canal. The disclosed ear tip piece also comprises a first channel passing through the solid portion for transmitting sound to the ear, and a second channel passing through the solid portion for allowing natural transmission of sound to the ear drum.

In another alternative embodiment, an ear tip piece for insertion in an ear canal to attenuate sound being transmitted to the ear is disclosed that comprises a first end including a solid portion that is sized and shaped to be inserted into an ear canal and a second end including a reversibly compressible portion for sealing the ear canal. The ear tip piece has a channel for transmitting sound to the ear and a sound attenuator fit inside the channel for attenuating sound being transmitted to the ear.

In yet another alternative embodiment, an ear tip piece for insertion in an ear canal to attenuate sound being transmitted to the ear is disclosed that comprises a first end including a solid portion that is sized and shaped to be inserted into an ear canal and a second end including a reversibly compressible portion for sealing the ear canal. The ear tip piece has a bend between the first end and second end, wherein the bend is positioned and shaped to facilitate insertion of the ear tip piece at or near a first or second bend of the ear canal. The ear tip piece also has a channel passing through the solid portion for transmitting sound to the ear and a sound attenuator to attenuate sound transmitted to the ear. The ear tip piece also has a coupler inserted into the channel for retaining the sound attenuator in the ear tip piece.

DETAILED DESCRIPTION OF THE INVENTION

Figure 1:
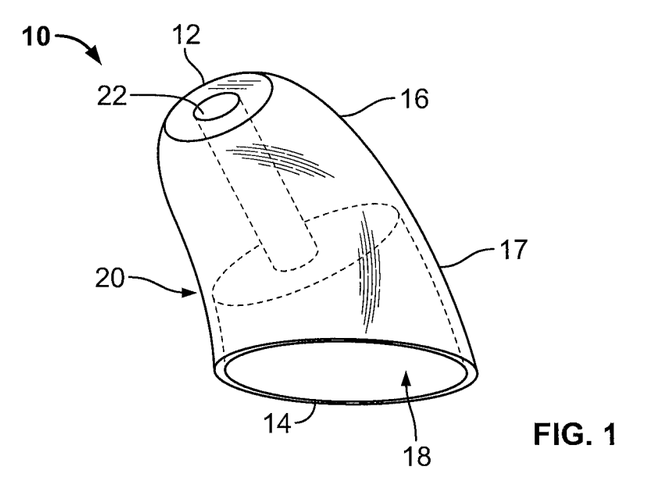
FIG. 1 is a perspective view of an ear tip piece according to one embodiment of the present invention, having a first channel for transmitting sound to the ear.
Figure 2:
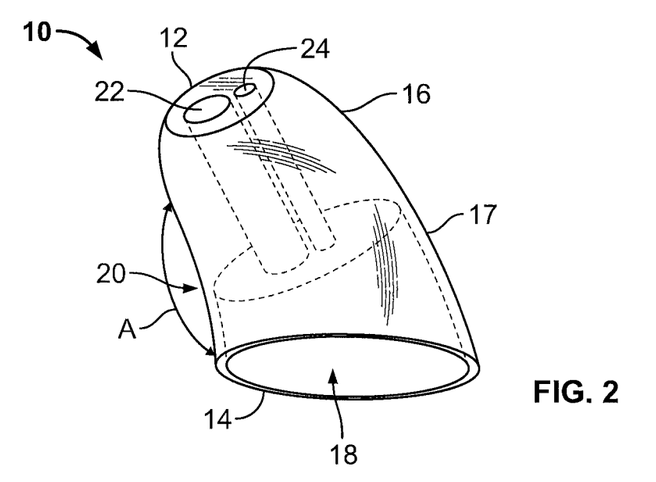
FIG. 2 is a perspective view of an alternative embodiment of an ear tip piece of the present invention, having a second channel used to allow the natural transmission of sound to the ear drum and pressure equalization.
Figure 3:
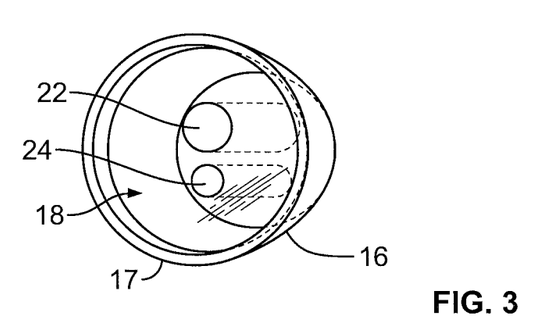
FIG. 3 is a rear perspective view of the ear tip piece of FIG. 2.

Referring to FIGS. 1-3, a left hearing aid ear tip piece 10 is shown having a first end 12 that includes a solid portion 16 that is sized and shaped to be inserted into an ear canal and a second end 14 that includes a reversibly compressible portion 17 that conforms to the shape of the ear canal to create a tight fit and secure the ear tip piece in the ear canal, and to seal the ear canal. In a preferred embodiment, the reversibly compressible portion 17 is hollow 18. In a further preferred embodiment, the ear tip 10 also has a bend 20. As best shown in FIG. 2, the bend 20 is preferably positioned between the first end 12 and the second end 14. The bend 20 begins at the second end 14 and becomes more pronounced as it moves to the first end 12. A first channel 22 is shown that passes through the solid portion 16 for transmitting sound to the ear. FIG. 2 shows a left ear tip piece having a second channel 24.

The ear tip piece is preferably made of a resilient material such as silicone or other materials known in the art, such as plastic, rubber, synthetic polymer or natural polymer. The ear tip piece is sized and shaped to be inserted within a human ear canal, which typically is elliptical in shape and has a smaller chord of between about 0.3 and 0.6 inches at the aperture of the ear canal. Between the first and second bends of the ear canal the smaller chord of the elliptical ear canal is generally from about 0.2 to 0.5 inches. In a preferred embodiment, the ear tip piece is approximately 0.48 inches long on the side having an interior curve with respect to the bend 20 and 0.59 inches on the opposite side. In an alternative embodiment, the ear tip piece is approximately 0.49 inches long on the side having an interior curve with respect to the bend 20 and approximately 0.60 inches on the opposite side. In a preferred embodiment, the ear tip piece is approximately 0.32 inches wide at the second end 14 and approximately 0.18 inches wide at the first end 12. In an alternative embodiment, the ear tip piece is approximately 0.36 inches wide at the second end 14 and approximately 0.27 inches wide at the first end 12.

The ear tip piece is inserted into a person's ear canal such that it is positioned close to the ear drum, preferably near or beyond the first or second sloping and/or narrowing of the ear canal, also referred to in the art as a bend. The shape of the disclosed ear tip piece preferably includes a bend 20. In a preferred embodiment, the bend forms an interior angle A of approximately 72°+/−15°. The bend 20 is preferably positioned and shaped to allow the ear tip piece to more closely approximate the shape of the ear canal, facilitating deeper insertion into the ear canal than can be accomplished with previous ear tip pieces, such as conventional dome shaped ear tip pieces. This allows the ear tip piece to be positioned closer to the ear drum, thereby reducing the air volume or acoustic mass present between the end of the ear tip piece and the ear drum. This air volume or acoustic mass must be moved during sound transmission to enable a person to hear. The smaller the acoustic mass, the less air volume that must be moved, which improves the wearer's hearing experience and comfort and lowers the corresponding hearing device amplification required to increase the sound pressure level at the ear drum. In addition, forming the first and second channels within the solid portion allows the channels to have a fixed angle relative to the ear tip piece, thereby permitting the channels to be more accurately directed toward the ear drum.

The solid portion 16 of the ear tip piece 10 provides a more rigid structure that helps the wearer properly align the ear tip piece in the ear canal. In a preferred embodiment, the solid portion 16 extends approximately 0.35 inches from the first end 12 toward the second end 14. The more rigid structure also provides tactile feedback to the wearer while the ear tip piece is being inserted into the ear canal, providing the wearer with the feeling that the device is traversing fully into the ear canal, is properly seated and will not fall out.

The solid portion 16 of the ear tip piece 10 also directs sound—such as sound produced by a conventional hearing aid speaker or receiver, as detected by a transducer and as transmitted through tubing fitted into the first channel 22—substantially toward the ear drum and not substantially into the side wall of the ear canal. In a preferred embodiment, this is partially accomplished via the bend 20 and the flexible nature of the reversibly compressible portion 17, which allows the ear tip piece to be compressed. This allows the ear tip piece to better follow the natural curve of the ear, which, when used in conjunction with a hearing aid, essentially guides the speaker or receiver, tubing, and/or coupler along the axis of the ear canal. Sounds delivered directly at the ear drum increase transmission efficiency to the middle ear system and improve a wearer's hearing. Conventional dome style tips or flaccid tips do not provide any guidance in positioning the receiver towards the ear drum at a proper angle and more effort has to be applied to shaping of the wire system, which is cumbersome due to the delicate wires and risk of breaking the contact points and causing a short in the wire.

Once inserted into the ear canal, the reversibly compressible portion 17 expands to conform to the shape of the ear canal, which secures the ear tip piece within the ear canal and creates a substantially tight seal within the ear canal. As can be seen in FIGS. 1-3, the second end 14 flares outward, such that it is wider than the first end 12. This also helps create a more effective seal of the ear canal. In some cases, a completely airtight sealing of the aperture of the ear canal may result in an occlusion effect, which causes an altered perception of one's voice while talking. By fitting deeper in the ear canal the ear tip piece takes up more space relative to the size of the ear canal and prevents a wearer's throat generated vocals from entering the ear canal by sealing off the cartilaginous portion where larynx generated transmissions enter the ear canal. Some wearers find this characteristic to be beneficial by reducing the occlusion effect, also described as "head in a barrel" or echo complaints and restoring a more natural sound to their voice.

The tight seal created by the reversibly compressible portion 17 of the ear tip piece also results in greater comfort and security to the wearer, by, for example, minimizing or eliminating vibrations caused by walking or other wearer movements. In a preferred embodiment where the ear tip piece is used in conjunction with a hearing device, when vibrations reach the hearing device through either the tubing or wire they can adversely affect sound quality and may cause or increase the tickle effect. The tickle effect generally occurs when only a few of the hairs that line the ear canal are engaged or contacted by an object, such as an ear tip piece. However, if a large surface area and a resultant large number of hairs are all pressed at the same time, the tickle effect is minimized or eliminated. The solid portion 16 and reversibly compressible portion 17 of the disclosed ear tip piece may be configured to create a substantial contact surface with the surface of the ear canal, reducing the tickle effect felt by a wearer.

In a preferred embodiment, the reversibly compressible portion 17 is formed by a hollow 18 that has relatively thin walls that facilitate compression and adaptation of the reversibly compressible portion to the shape of the ear canal. In a particularly preferred embodiment, the walls of hollow 18 range in thickness from about 0.03 inches to 0.05 inches thick and, in an alternative embodiment, range from about 0.05 inches to 0.07 inches thick. In a particularly preferred embodiment, the walls of the hollow 18 of reversibly compressible portion 17 are approximately 0.02 inches thick. The size of the hollow 18 reversibly compressible portion 17 is may be adjusted to fit an individual ear by trimming. For example, the hollow 18 reversibly compressible portion 17 may be trimmed using a pair of scissors or any other suitable means, to remove any portion of the ear tip piece that protrudes outside of a wearer's ear canal. This enables the ear tip piece to be customized to an individual wearer.

As shown in FIG. 1, a first channel 22 allows sound transmission between the ear drum and an environment outside the ear. Alternatively, the first channel 22, in FIG. 1 can be used to fit a speaker or receiver of a hearing aid system, used to deliver amplified sound to the ear drum.

FIG. 2 depicts a further embodiment that also has a second channel 24. The second channel 24 may be used for venting, which allows natural transmission of unamplified sound between the ear drum of a wearer and an environment outside the ear, as occurs when no ear tip piece or hearing device is inserted into the wearer's ear canal. This tends to help alleviate the occlusion effect, where a wearer's voice sounds altered and possibly echoes, by allowing sound to traverse naturally to and from the ear. When used in conjunction with a hearing aid, such venting may vary the gain in the ear canal created by the amplified sound produced by the speaker or receiver. The unamplified natural sound transmitted through the second channel 24, depicted as a vent in FIG. 2, may combine with the amplified sound, which may either constructively and/or destructively interfere with the unamplified vented sound. Altering the width of the vent can reduce, in many cases, the amount of feedback or whistling that may occur as a result of the amplified sound looping back to the microphone or transducer of the hearing aid and, in other cases, can make the hearing aid sound warmer due to the increased amplification achieved. The warmer or improved sound quality is typically achieved by either lessening the occlusive effect experienced by the wearer or by increasing the insertion loss or seal created by the ear tip piece, resulting in increased amplification. The size of the second channel 24 can be adjusted by adding a separate vent plug (not shown) that changes the width of the channel.

Figure 6:
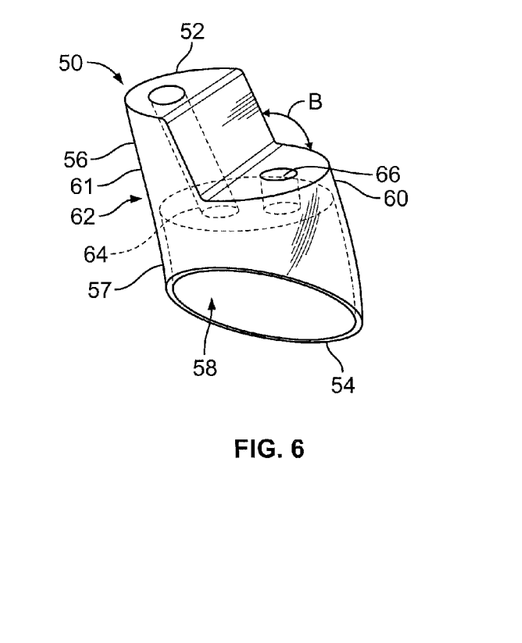
FIG. 6 is perspective view of another alternative embodiment of an ear tip piece of the present invention having a solid portion that has a base and a projection.

The first channel 22 and the second channel 24 can be a variety of widths, shapes, or slopes to allow for various tubes, receivers and monitors to be fit therein by friction or other known methods. In an embodiment, the width of the first channel 22 ranges from approximately 0.06 inches to 0.13 inches and in a preferred embodiment is approximately 0.10 inches wide. In a further embodiment, the second channel 24 ranges in width from about 0.02 inches to 0.13 inches and in a preferred embodiment is approximately 0.09 inches wide. The first and second channels may be parallel or arranged at different angles to each other, as best shown in FIG. 6. For example, the slope of the first channel 22 may be designed to direct the transmission of sound toward a wearer's ear drum. The first and/or second channel may have threaded interior surfaces to facilitate coupling to various sized tubes, receivers and monitors.

In an alternative embodiment, the second channel 24 may be used to insert a probe microphone to perform a real ear hearing test on a wearer while using a hearing aid. The probe microphone measurement or real ear measurements allow the function of a hearing aid to be tested while it is being worn. The results of the real ear hearing test allow adjustments to be made to ensure optimal amplification of sound when the hearing aids are being worn. Such real ear measurements can be used to identify variations caused by the anatomy of the particular wearer.

FIG. 3 depicts a rear view of the ear tip piece, showing the solid portion 16, the reversibly compressible portion 17, a first channel 22 and a second channel 24. In FIG. 3, the reversibly compressible portion 17 of the embodiment is hollow 18 and oval-shaped in cross-section. The oval shape and flare of the reversibly compressible portion 17 facilitates the adaptation to the shape and creation of a seal within the ear canal.

In an alternative embodiment, the second end 14 that includes the reversibly compressible portion 17 is oval shaped in cross-section, such as an ellipse, to more closely conform to the shape of the ear canal. In a preferred embodiment, the second end 14 is elliptical shaped in cross-section, the short chord of the ellipse ranging from about 0.31 inches to about 0.36 inches and the long chord of the ellipse ranging from about 0.49 inches to about 0.59 inches, +/−0.05 inches. In a particularly preferred embodiment, the short chord of the elliptical cross-section of second end 14 is about 0.31 inches and the long chord is about 0.50 inches, +/−0.05 inches. In an alternative particularly preferred embodiment, the short chord of the elliptical cross-section of the second end 14 is about 0.36 inches and the long chord is about 0.59 inches, +/−0.05 inches.

In an alternative embodiment, the first end 12 is oval shaped in cross-section. In a preferred embodiment, the first end 12 is elliptical in cross-section, the short chord of the ellipse ranging from about 0.18 inches to about 0.27 inches and the long chord of the ellipse ranging from about 0.26 inches to about 0.36 inches, +/−0.05 inches. In a particularly preferred embodiment, the short chord of the elliptical cross-section of the first end 12 is about 0.18 inches and the long chord is about 0.26 inches, +/−0.05 inches. In an alternative embodiment, the short chord of the elliptical cross-section of the first end 12 is about 0.27 inches and the long chord is about 0.36 inches, +/−0.05 inches.

Figure 4:
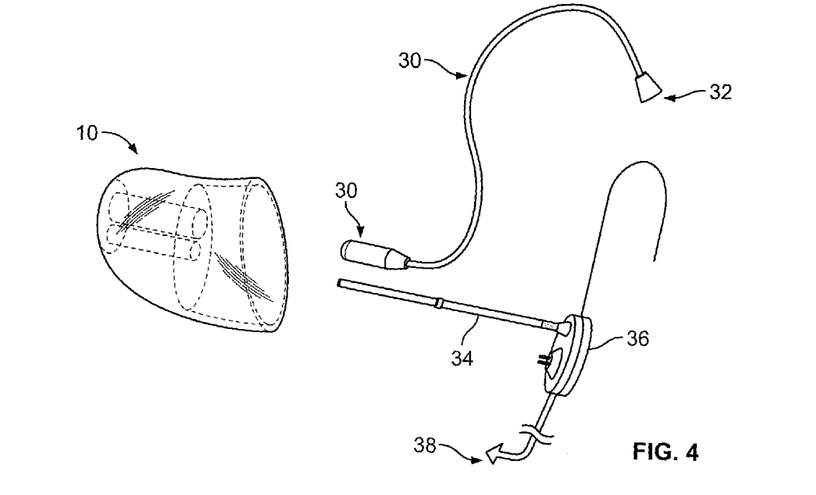
FIG. 4 is a schematic view of an application for using the ear tip piece of FIG. 2 with RIC (receiver in canal) hearing aid unit and real ear measurement probe tube thereof.

FIG. 4 depicts an embodiment of a left ear tip piece 10 being used with an RIC hearing aid. The speaker or receiver 30 is positioned inside the first channel, e.g. sized and shaped to friction fit within the channel, in the ear tip piece and connected to a RIC hearing aid via a connector 32. In a two channel embodiment, as shown in FIG. 4, a probe tube 34 is positioned inside a second channel and attached to a probe microphone 36. Probe microphone or real ear measurements received from the probe microphone 36 are sent to a monitor system 38 to enable an audiologist to assess the functionality of a wearer's hearing aids as is known in the art.

Figure 5:
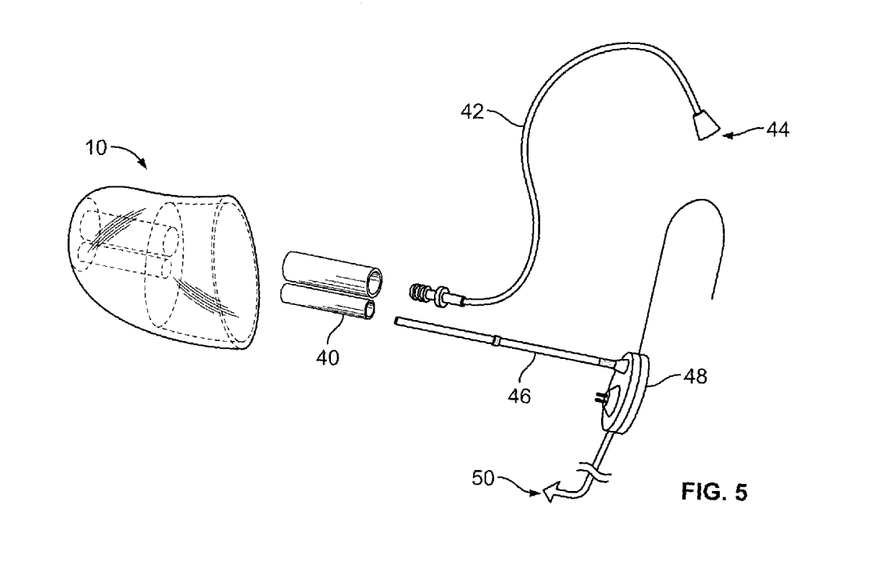
FIG. 5 is a schematic view of an application for using the ear tip piece of FIG. 2 with OTE (over the ear) thin tube used in conjunction with a hearing aid and real ear measurement probe tube thereof and coupler.

Similarly, FIG. 5 depicts an embodiment of a left ear tip piece 10 being used with an OTE or BTE hearing aid. In this embodiment a coupler 40 is used to adjust the width of the first channel to allow connection of a thin tube 42 to the ear tip piece 10. The thin tube 42 is then connected to an OTE/BTE hearing aid via a connector 44. The coupler 40 may also be used to connect the probe tube 46 to the ear tip piece 10. The probe microphone 48 is connected to the probe tube 46 and sends data to a monitor system 50.

The coupler 40 is preferably made of a more rigid material than the ear tip piece, such as plastic, and functions to narrow the width of the first channel and/or second channel to enable various tubes or other items to be coupled to the ear tip piece. The coupler 40 may be fixed within the channel by glue, friction fit, or fit via a barbed interface. In a preferred embodiment, the coupler 40 is a tubular piece of rigid material, preferably cylindrical, having a channel extending through the center and having barbs on the exterior surface to allow it to be fit inside a single channel in the ear tip piece. In an alternative embodiment, the coupler (not shown) comprises two of the tubular pieces described above that are joined together at an outer surface and configured to be inserted inside both channels of a two channel embodiment of the ear tip piece. In addition, the interior surface of the coupler's channel may be provided with threads (not shown) to facilitate coupling of a device, such as a hearing aid, to the coupler and insertion of the coupler and device into the ear tip piece channel. Couplers can come in a variety of materials, shapes and sizes. By having a variety of couplers available for use when coupling different materials and/or devices to the ear tip piece, this allows the same ear tip piece to be used with a variety of hearing aids or other systems, resulting in a reduction in inventory.

In a preferred embodiment, the ear tip piece is easily removed from the receiver or tubing inserted into the first or second channel, as, for example, shown in FIGS. 4 and 5, and is washable.

Figure 8:
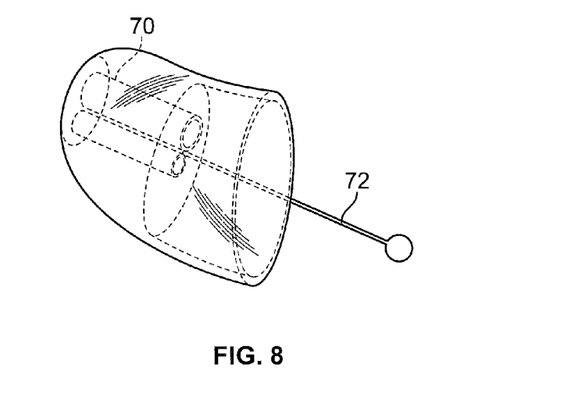
FIG. 8 is a perspective view of yet another alternative embodiment of an ear tip piece of the present invention showing couplers inserted in the first and second channels and an extraction string coupled to the couplers.

In an alternative embodiment of a left ear tip piece shown in FIG. 8, a coupler 70 may also be used to facilitate coupling of an extraction device, such as an extraction string 72, system, or lanyard. In a preferred embodiment, the extraction string is made of any suitably strong, thin material, such as fishing wire or a filament. The extraction string 72 may be fixed to the coupler 70 by gluing or other methods known in the art.

Figure 7:
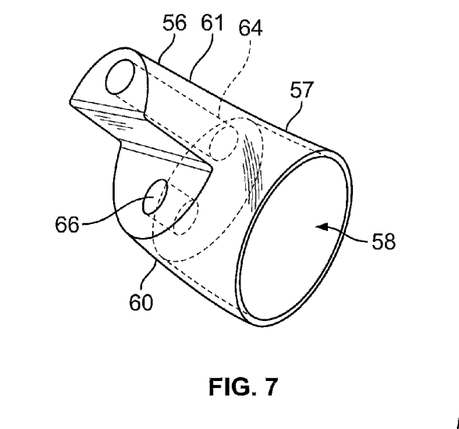
FIG. 7 is a top perspective view of an alternative embodiment of the ear tip piece of FIG. 6 having a base and a projection positioned at a different angle.

FIGS. 6 and 7 show an alternative embodiment of the ear tip piece 50, having a first end 52 including a solid portion 56 that is sized and shaped to be inserted into an ear canal and a second end 54 including a reversibly compressible portion 57 for sealing the ear canal. FIG. 6 shows a left ear tip piece and FIG. 7 shows a right ear tip piece. In the embodiment depicted in FIGS. 6 and 7 the reversibly compressible portion 57 is hollow 58. The ear tip piece 50 has a bend 62 between the first end 52 and the second end 54. The bend 62 extends upward from the second end 54 to the first end 52. The ear tip piece also has a first channel 64 and a second channel 66. In this embodiment, the solid portion 56 comprises a base 60 and a projection 61 that are positioned at an angle to one another B. Different angles between base 60 and a projection 61 may be used to better adapt the ear tip piece to the contour of the ear canal and/or direct the first channel toward the ear drum, as illustrated by comparison of FIGS. 6 and 7. In a preferred embodiment shown in FIG. 6, the base 60 and projection 61 form an interior angle B of about 105°+/−15°. The projection 61 extends from the base and the first channel 64 passes through the projection. The projection 61 of the solid portion 56 has a narrower width than the base 60 and is preferably just large enough to cover a speaker or receiver unit, tubing, coupler, or other material inserted in the first channel 64. This provides the smallest sized ear tip piece 50 and allows the ear tip piece to be inserted at the deepest and most narrow shape of the canal.

The base 60 and projection 61 ear tip piece embodiment reduces the occlusion effect by using less solid mass in the ear canal, and it provides less mass at the tip of the device where many ear canals begin to narrow. This increases the percentage of ear canals that can be fit. Further, the base 60 and projection 61 create an angle that facilitates the insertion of the ear tip piece into the ear canal as it follows the contour of the ear towards the ear drum. This angle allows the ear tip piece to follow the contour deeper into the ear canal than conventional ear tip pieces.

The embodiment shown in FIG. 6 provides a second channel 66 used for venting, discussed above, which remains unobstructed thereby reducing the occlusive effect. The second channel 66 passes through the base 60. When the venting channel is left unobstructed, unamplified sound can reach the eardrum directly, and improve the natural sound quality heard by patients with normal or mild hearing loss in the low frequencies. Simultaneously, the total acoustic mass of the ear canal has still been reduced (effective ear canal volume has been decreased) causing corresponding insertion loss. The tradeoff benefit to insertion loss, is the fact that less air pressure is required to reach the same levels of gain, increasing the added stable gain.

Figure 9:
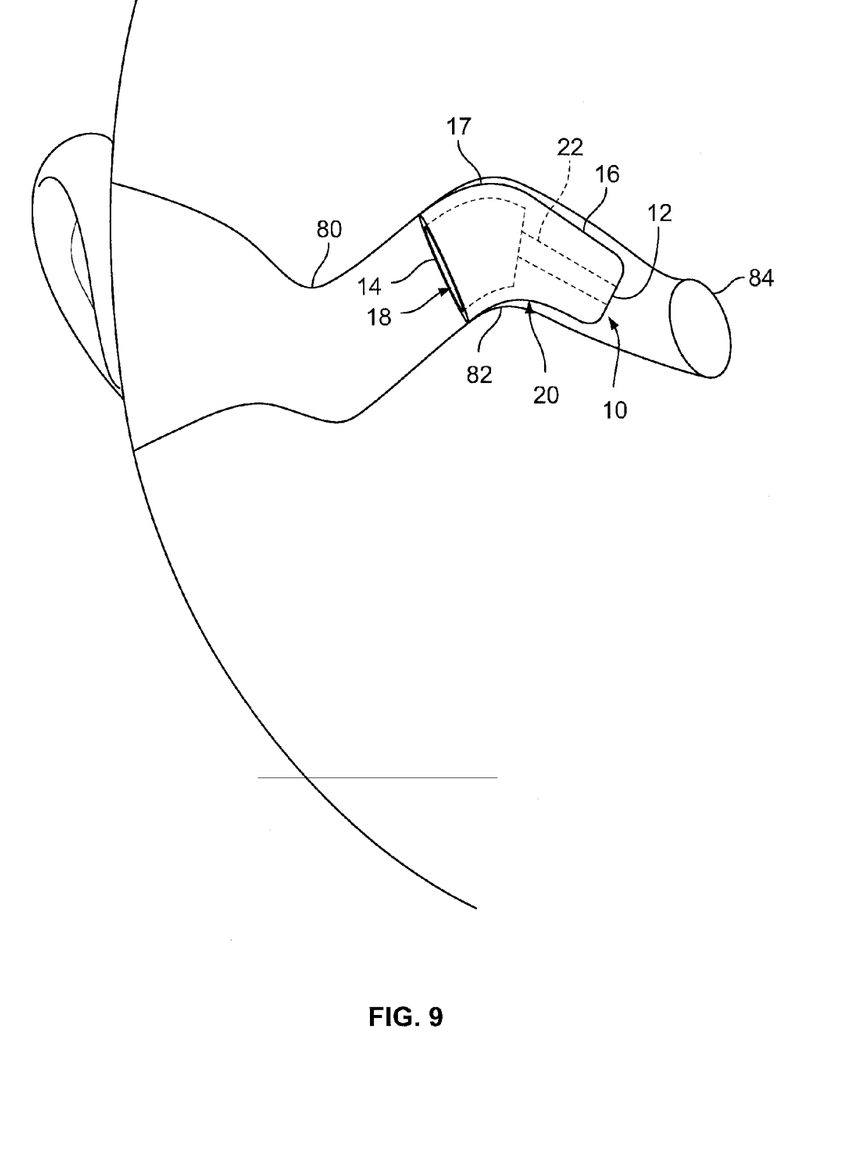
FIG. 9 is a top view of a human ear canal showing an embodiment of an ear tip piece inserted into the ear canal.

FIG. 9 depicts a right ear tip piece 10 inserted into a human ear canal, shown from a top view, having a first bend 80 and a second bend 82. The ear tip piece 10 has a first end 12 including a solid portion 16 sized and shaped to be inserted into an ear canal and a second end 14 including a reversibly compressible portion 17 for sealing the ear canal. The depicted ear tip piece 10 has a bend 20 for facilitating insertion of the ear tip piece and a first channel 22 for transmitting sound to the ear. The reversibly compressible portion 17 is preferably hollow 18. As shown in FIG. 9, the reversibly compressible portion 17 becomes compressed against the walls of an ear canal, adapting to the shape of the ear canal to create a seal.

Bend 20 is preferably positioned and shaped to facilitate insertion of the ear tip piece at or near the first bend 80 or, alternatively, the second bend 82. The ear tip piece 10 shown in FIG. 9 is inserted at or near the second bend 82 in close proximity to the ear drum 84. The positioning of the ear tip piece 10 in close proximity to the ear drum 84 reduces the size of the acoustic mass or air volume that must be moved to stimulate the ear drum, resulting in an improved hearing experience for the wearer and, when used with a hearing aid, reducing the amplification required to increase the sound pressure level at the ear drum. Because first channel 22 is formed in solid portion 16, its angle relative to the ear tip piece is fixed, allowing the first channel to be directed at ear drum 84.

Those of skill in the art will appreciate that, in addition to being used with RIC, OTE or BTE hearing aids, the claimed ear tip piece can be adapted for use in conjunction with stethoscopes, MP3/IPOD/Digital audio players, or sound recording devices. The ear tip piece can also be used with a sound blocking ear plug or a swimmer's ear plug.

Figure 10:
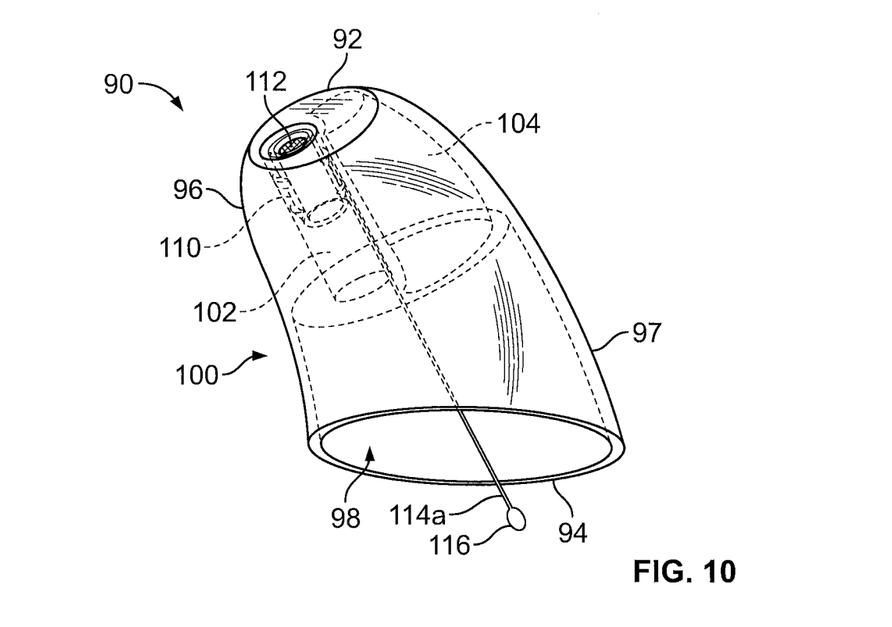
FIG. 10 is a perspective view of an ear tip piece according to one embodiment of the present invention, having a coupler retaining a sound attenuator inserted into a channel to reduce sound being transmitted to the eardrum and an extraction device.

FIG. 10 shows an embodiment of a left ear tip piece 90 having a first end 92 including a solid portion 96 that is sized and shaped to be inserted into an ear canal and a second end 94 including a reversibly compressible portion 97. The reversibly compressible portion 97 is hollow 98. The ear tip piece 90 has a bend 100 between the first end 92 and the second end 94. The bend 100 extends from the second end 94 up to the first end 92. The ear tip piece also has a channel 102. The ear tip piece has a cavity 104 in the solid portion 96 adjacent to the channel 102 that does not extend through the first end 92 of the ear tip piece 90. In the embodiment shown in FIG. 10, a coupler 110 is inserted in the channel 102. The coupler 110 retains a sound attenuator 112 to reduce or attenuate the decibel level of sound that reaches a wearer's eardrum. Additionally, the coupler 110 is used to facilitate coupling of an extraction device 114a to aid with removal of the ear tip piece 90. In FIG. 10 the extraction device 114a extends straight outward from the coupler and has a ball 116 at the end to facilitate grasping the extraction device 114a and pulling to remove the ear tip piece from a wearer's ear canal. In a preferred embodiment, the ball 116 is 1/16 inch in diameter.

The ear tip piece 90 is preferably made of a resilient material such as silicone, vinyl, rubber, plastic, synthetic polymer or natural polymer, as indicated above, but can be made with other suitable materials known in the art. In a particularly preferred embodiment, the ear tip piece 90 is made of a styrene block copolymer compound called VERSALFLEX™ CL30 manufactured by GLS Corporation in McHenry, Ill.

In a preferred embodiment, the channel 102 is approximately 0.30 inches long and 0.10 inches in diameter.

Figure 11:
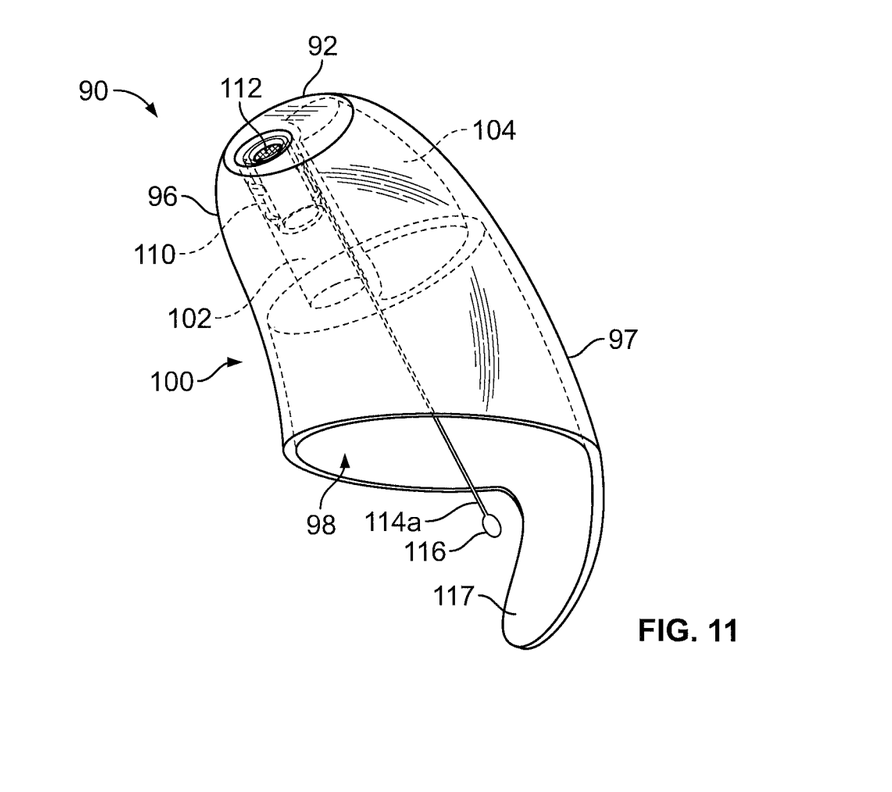
FIG. 11 is a perspective view of an alternative embodiment of an ear tip piece, having a coupler retaining a sound attenuator inserted into a channel to reduce sound being transmitted to the ear, an extraction device and an extraction flap.

FIG. 11 shows an alternative embodiment of the left ear tip piece shown in FIG. 10 that has a flap 117. The flap 117 is an extension of the reversibly compressible portion 97 of the ear tip piece that is flexible. The flap 117 can be present in combination with an extraction device 114a, as shown in FIG. 11. However, the flap 117 is not limited to being present with any particular combination of features of the ear tip piece. The flap 117 can be grasped by a wearer and used to facilitate removal of the ear tip piece from the ear canal. Alternatively, the flap 117 can act as a concha lock, which is known in the industry, that prevents the ear tip piece from slipping out of the ear canal, typically due to excessive movement, such as that associated with TMJ.

Figure 12:
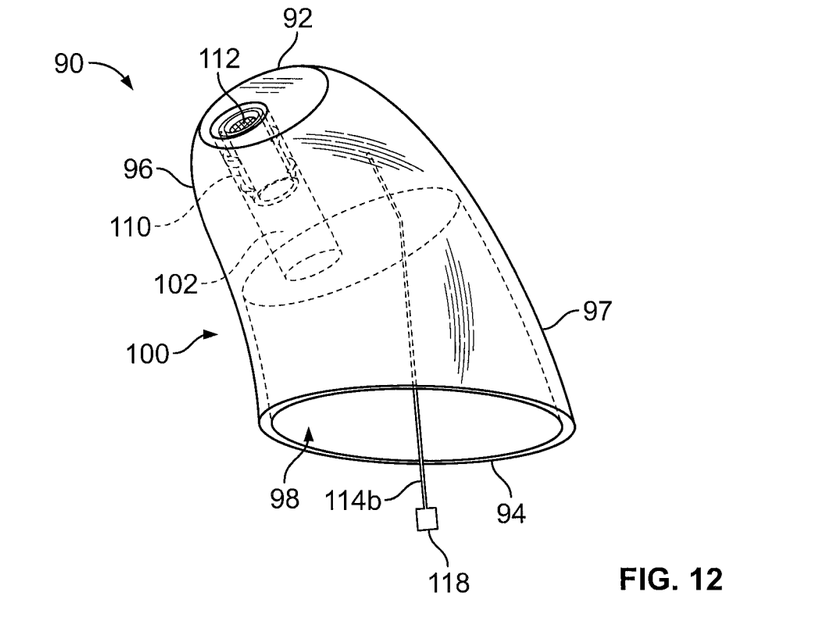
FIG. 12 is a perspective view of an alternative embodiment of an ear tip piece, having a coupler retaining a sound attenuator inserted into a channel to attenuate sound being transmitted to the ear and an alternative embodiment of an extraction device.

FIG. 12 shows another alternative embodiment of the left ear tip piece shown in FIGS. 10 and 11. In this alternative embodiment, the solid portion 96 of the ear tip piece has a channel 102, but does not have a cavity adjacent the channel 102. This provides an alternative embodiment of the extraction device 114b where the extraction device 114b is inserted into the solid portion 96 of the ear tip piece 90 independent of the coupler 110. The portion of the extraction device 114b that is inserted into the solid portion 96 of the ear tip piece 90 is shaped so that the extraction device 114b is not pulled out of the ear tip piece when it is pulled on by the wearer. In an embodiment, the portion of the extraction device 114b inserted into the solid portion 96 has a greater diameter than the rest of the extraction device. In an alternative embodiment shown in FIG. 12, the extraction device 114b is bent or angled as it exits the solid portion 96 and enters the reversibly compressible portion 97 of the ear tip piece 90. The extraction device 114b can be bent or angled at any angle appropriate for facilitating grasping of the extraction device 114b to aid in the removal of the ear tip piece from the ear canal. Additionally, the extraction device 114b has a flat plane 118 at the end to aid with a wearer's orientation of the ear tip piece in the ear canal and to also facilitate removal of the ear tip piece from the ear canal. The end of the extraction device 114*b* is not limited to the disclosed embodiments and can be any size and shape that is reasonable to assist with orientation and extraction of the ear tip piece in a wearer's ear canal.

Figure 13:
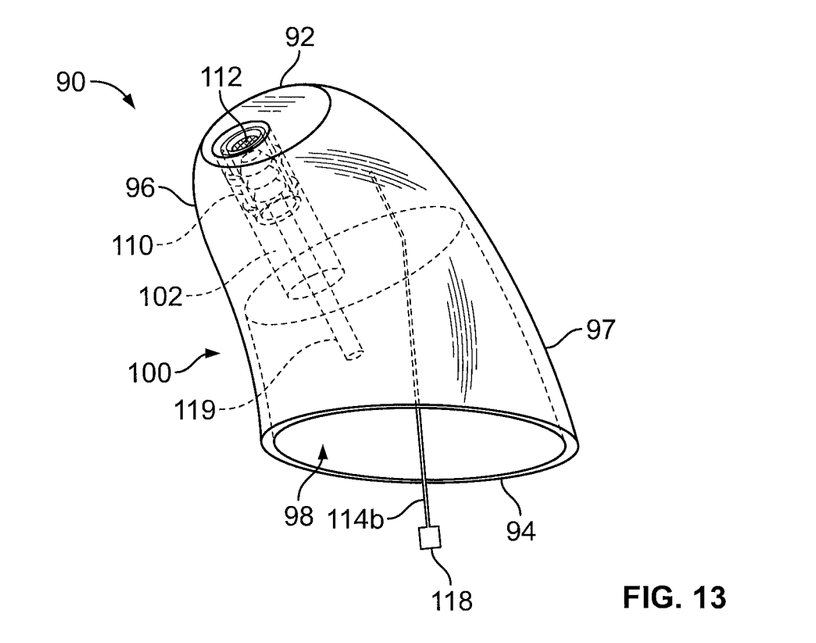
FIG. 13 is a perspective view of an alternative embodiment of an ear tip piece, having a coupler retaining a sound attenuator inserted into a channel to attenuate sound being transmitted to the ear, an extraction device and an insertion device.

FIG. 13 shows an alternative embodiment of the left ear tip piece shown in FIG. 12, having an insertion device 119 that extends the area a wearer can apply longitudinal force to when inserting the ear tip piece in his or her ear canal, facilitating insertion of the ear tip piece 90. In a preferred embodiment, the insertion device 119 is a cylinder that has a channel to allow transmission of sound through the ear tip piece. The insertion device can be made of any suitable material known in the industry, such as plastic or other polymers.

In an embodiment, the insertion device 119 is fixed or coupled to the coupler 110, which can be done by inserting the insertion device 119 into the coupler 110 and retaining the insertion device 119 in place in the coupler 110 by friction fitting or gluing. Alternative manners of coupling the insertion device to the coupler known in the industry can also be used. In an alternative embodiment, the insertion device 119 has barbs (not shown) or flanges that facilitate friction fitting it into the coupler 110. In an further alternative embodiment, the inside of the coupler's channel can be threaded with a female mate to barbs or grooves on the insertion device.

In an alternative embodiment, the insertion device is fixed or coupled to the ear tip piece independent of the coupler (not shown) using any appropriate known method, such as friction fitting or gluing. In a further alternative embodiment, the insertion device is an elongated coupler that extends into the reversibly compressible portion 97 of the ear tip piece. In a preferred embodiment, the insertion device 119 extends past the solid portion 96 of the ear tip piece 90 into the reversibly compressible portion 97, but does not extend past the second end 94 of the ear tip piece 90. However, any appropriate length can be used that does not inhibit a wearer's ability to insert or wear the ear tip piece, or impair the transmission of sound.

Figure 14:
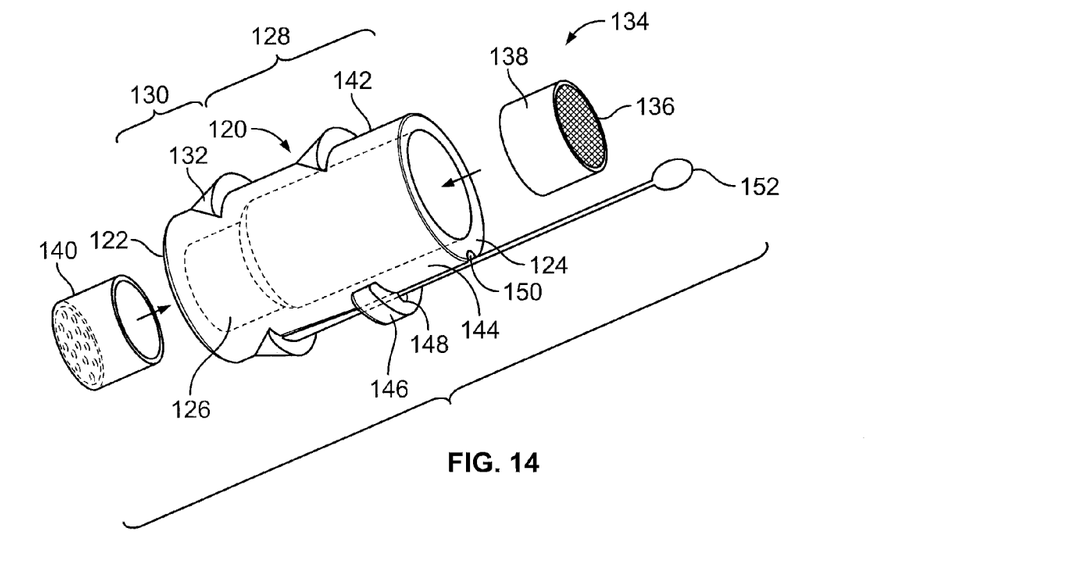
FIG. 14 is an exploded view of a an embodiment of a coupler retaining a sound attenuator to attenuate sound being transmitted to the ear and an wax basket to prevent buildup of ear wax.
Figure 15:
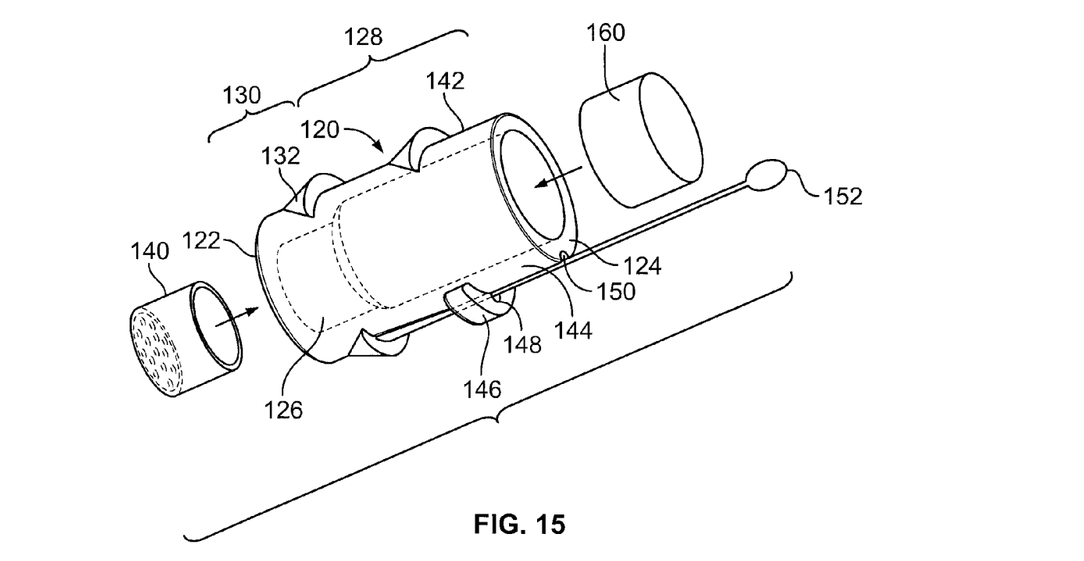
FIG. 15 is an exploded view of an alternative embodiment of a coupler retaining a sound attenuator to attenuate sound being transmitted to the ear and a wax basket to prevent buildup of ear wax.

FIGS. 14 and 15 show an exploded view of an embodiment of a coupler 120. The coupler 120 has a first end 122 and a second end 124. A channel 126 runs through the coupler 120 and has a narrow portion 130 and a wide portion 128. The coupler 120 has a first wall 142 and a second wall 144. The first end 122 has a flange (not shown) that holds a wax basket 140 in place inside the narrow portion 130 of the channel 126 of the coupler 120. A sound attenuating element 134 is friction fit inside the wide portion 128 of the coupler's channel 126. The coupler 120 has barbs 132 on its outside surface for use when friction fitting the coupler 120 into the first channel of an ear tip piece. The coupler 120 also has a rounded barb 146 that has a channel 148. A trough 150 on the coupler passes under the channel 148 in the rounded barb 146 and allows an extraction device 152 to be threaded through the channel 148 and fixed into the trough 150 via gluing or any other suitable means.

The coupler 120 is preferably made of more rigid material than the ear tip piece, such as plastic, polymeric plastic, acrylic, or any other suitable material known in the art. In a particularly preferred embodiment, the coupler 120 is made of a methacrylic material called FotoTec® SL.A manufactured by Dreve Otoplastik GmbH in Unna, Germany.

The size of the coupler 120 is dictated in part by the ability of the channel to be able to continue to transmit sound without changing the frequency of the sound or resonating the sound. Generally, channels with diameters less than 0.020 inches alter or inhibit the transmission of sound; thus, channels with diameters greater than 0.040 inches are typically preferred. In a preferred embodiment, the coupler 120 is approximately 0.280 inches long and approximately 0.13 inches wide. The diameter of the channel 126 at the first end 122 is approximately 0.067 inches. The length of the narrow portion 130 of the channel 126 is approximately 0.12 inches. The thickness of the first wall 142 at the first end 122 and extending through the narrow portion 130 of the channel 126 is approximately 0.036 inches. The thickness of the second wall 144 at the first end 122 and extending through the narrow portion 130 of the channel 126 is approximately 0.027 inches. The diameter of the channel 126 at the second end 124 is approximately 0.085 inches. The length of the wide portion 128 of the channel 126 is approximately 0.16 inches. The thickness of the first wall 142 at the second end 124 and extending through the wide portion 128 of the channel 126 is approximately 0.018 inches. The thickness of the second wall 144 at the second end 124 and extending through the wide portion 128 of the channel 126 is approximately 0.012 inches. The disparity in thickness between the first wall 142 that extends through the narrow portion 130 of the channel 126 (0.027 inches) and the first wall 142 that extends through the wide portion 128 of the channel 126 (0.018 inches) creates a ledge that holds the sound attenuator 134 in place in the wide portion 128 of the channel 126. In a preferred embodiment, the sound attenuator 134 is friction fit inside the channel 126 of the coupler 120. However, any suitable means of fitting and securing the sound attenuator 134 in the channel 126 known in the industry can be used, such as by gluing. In an alternative embodiment, the channel 126 of the coupler 120 has a uniform diameter (not shown) into which a sound attenuator 134 can be friction fit with or without a similarly friction fit wax basket 140.

In a preferred embodiment shown in FIG. 14, the wax basket 140 used is a Hear Clear wax protector manufactured by Starkey® in Eden Prairie, Minn. The wax basket 140 is approximately 0.055 inches long and has a diameter of approximately 0.067 inches. Any wax basket or wax protector of an appropriate size can be used in the coupler. In a preferred embodiment, the wax basket 140 is friction fit inside the coupler 120. Any other appropriate manner of fitting the wax basket 140 inside the channel known in the industry can be used.

In a preferred embodiment shown in FIG. 14, the sound attenuator 134 is comprised of a filter 136 or damper that is fit inside a casing 138. In a particularly preferred embodiment the filter is a white BF-1859-000 680 ohm acoustic damper with an acoustic casing manufactured by Knowles based in Itasca, Ill. The combined filter 136 and casing 138 is approximately 0.096 inches long and approximately 0.082 inches in diameter. Other materials known in the industry that attenuate sound can be used as the sound attenuator, such as foam, lamb's wool, plastic or silicone. In an alternative embodiment, the filter is inserted into the channel 126 of the coupler 120 without a casing. In a further alternative embodiment, the sound attenuator is positioned inside the ear tip piece's channel without use of a coupler. In a preferred embodiment the sound attenuator is positioned inside the ear tip piece's channel as close as possible to the first end of the ear tip piece, placing the sound attenuator in close proximity to the eardrum.

In a particularly preferred embodiment, the filter 136 and casing 138 are preassembled. In a further particularly preferred embodiment, the assembled sound attenuator 134 is then friction fit into the channel of the coupler. Other appropriate means of securing the sound attenuator 134 in the channel 126 known in the industry can be used, such as gluing. The sound attenuator 134 can be retained at any point in the channel 126 of the coupler 120. In a particularly preferred embodiment, the sound attenuator 134 is retained in the coupler's channel 126 as close to the first end 122 as possible. In this manner, the sound attenuator is placed in close proximity to the eardrum. In an alternative embodiment, the sound attenuator is replaceable and can be easily removed and replaced by a wearer.

In an alternative embodiment shown in FIG. 15, the sound attenuator is a plug 160 that is friction fit inside the coupler to achieve a greater reduction in sound than can be achieved with a filter or damper. The plug can be made of any material suitable for attenuating or blocking sound, such as foam, plastic or silicone.

Figure 16:
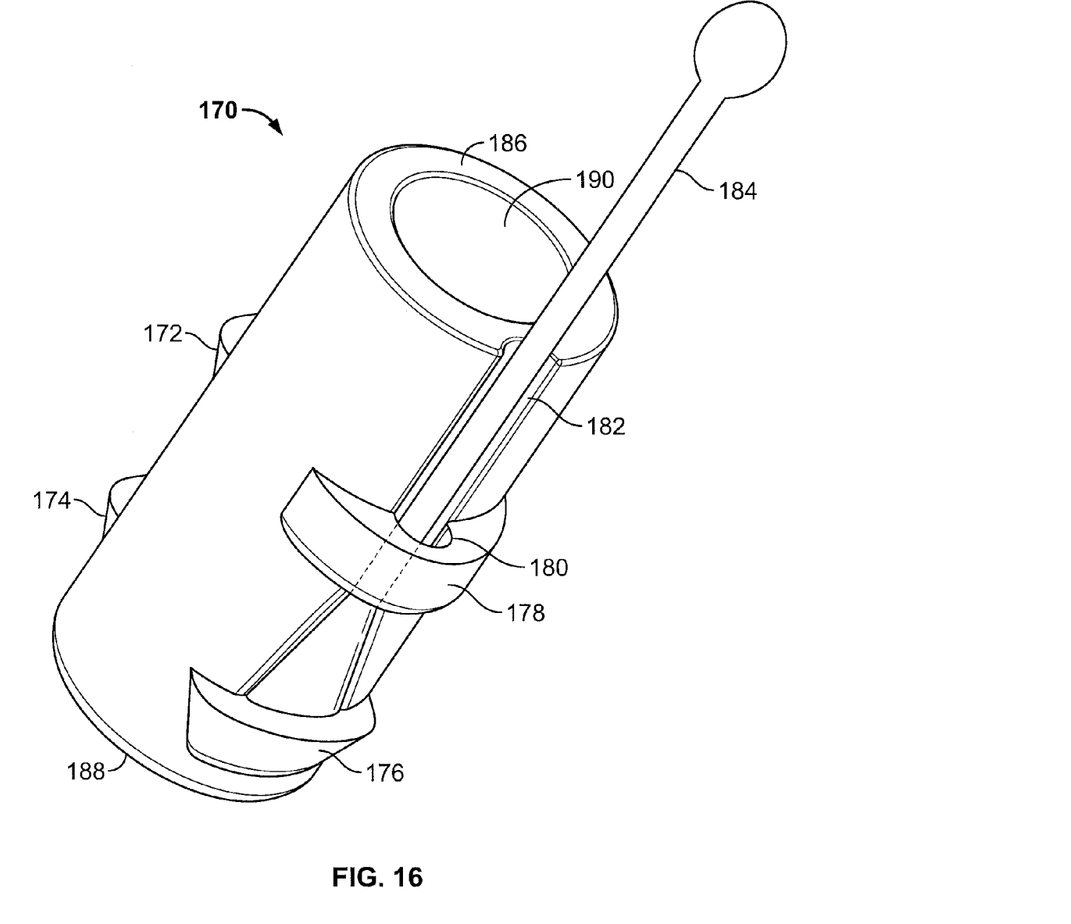
FIG. 16 is a perspective view of an embodiment of a coupler having an extraction device.

FIG. 16 shows a perspective view of an embodiment of a coupler 170. The coupler 170 has a first end 188 and a second end 186. In a preferred embodiment, the coupler 170 has a first barb 172, a second barb 174, a third barb 176, and a rounded barb 178 to assist with friction fitting the coupler 170 in a first channel of an ear tip piece. In a particularly preferred embodiment, the first 172, second 174 and third 176 barbs are angled, forming a peak that is the highest point away from the surface of the coupler. Other methods or interfaces commonly known and used for friction fitting can also be used to position the coupler inside the ear tip piece's channel. Additionally, methods other than friction fitting, such as gluing, can be used to position the coupler inside the ear tip piece's channel.

In a preferred embodiment, the first and second barb 172, 174 are approximately 0.040 inches long and approximately 0.012 inches high. The peak of the first barb 172 is located approximately 0.12 inches from the second end 186 of the coupler and approximately 0.10 inches away from the peak of the second barb 174. The peak of the second barb 174 is located approximately 0.060 inches away from the first end 188 of the coupler 170. The peak of the third barb 176 is also located approximately 0.060 inches away from the first end 188 of the coupler 170. The third barb 176 is approximately 0.040 inches long and approximately 0.015 inches high. Any appropriately sized barbs or other friction fitting interface can be used to friction fit the coupler 170 into the ear tip piece's channel.

The rounded barb 178 is centered approximately 0.12 inches from the second end 186 of the coupler 170. The rounded barb 178 has a channel 180 under which there is a trough 182 that begins at the second end 186 of the coupler 170 and continues to the peak of the third barb 176. The trough 182 has a diameter of approximately 0.015 inches and a width of approximately 0.024 inches from the second end 186 through the rounded barb 178. The channel 180 in the rounded barb 178 has a diameter of approximately 0.021 inches and a width of approximately 0.020 inches. The height of the rounded barb 178 measured from the trough 182 is approximately 0.033 inches, 0.018 inches of which extend above the surface of the coupler 170. The trough 182 from the rounded barb 178 to the peak of the third barb 176 flattens out to a width of approximately 0.060 inches and length of approximately 0.060 inches.

In a preferred embodiment, the extraction device 184 is fishing line having a diameter of 0.018 inches and passing a 20 pound test. In a particularly preferred embodiment, a piece of fishing line 1¾ inches long is cut, having one end blunted and the other end angled. The fishing line is threaded through the channel 180 in the rounded barb 178. The last ¹⁄₁₆ inch of the blunt end is flattened either before or after threading the fishing line through the channel 180. The fishing line is pulled tight and the flattened end is positioned in the portion of the trough 182 that extends from the rounded barb 178 to the peak of the third barb 176. The round portion of the fishing line is positioned in the remaining portion of the trough 182. In a particularly preferred embodiment, glue, preferably Pacer 50, Loctite 401, or Loctite 420, or any other suitable adhesive, and polymer powder is applied to the trough 182 between third barb 176 and rounded barb 178 to affix the extraction device 184 to the coupler 170. In a preferred embodiment, approximately 0.16 inches of the extraction device 184 is glued onto the coupler 170. In a preferred embodiment, the extraction device 184 is trimmed to a length of ⁵⁄₁₆ inch from the second end of the ear tip piece. In an alternative embodiment, the extraction device is molded as part of the coupler (not shown). In an alternative embodiment, the size or diameter of the extraction device increases as the extraction device extends past the coupler toward the second end of the ear tip piece to provide more tactile grip for a wearer.

Experimental Data

Ear tip pieces shown in FIG. 10, having the coupler shown in FIG. 14 without the wax basket, were sent for attenuation testing. The attenuation data were obtained in accordance with ANSI Standard S3.19-1974 in an independent university testing laboratory at Virginia Tech. Ten pairs of the above mentioned ear tip pieces were used in a study of 10 participants, 5 male and 5 female. The participant age range was from 26 to 43 years old with a mean age range of 32.4 years. The results of tests from thirty trials are set forth in the chart below.

|  | ⅓ octave band center (Hz) | | | | | | | | |
| --- | --- | --- | --- | --- | --- | --- | --- | --- | --- |
|  | 125 | 250 | 500 | 1000 | 2000 | 3150 | 4000 | 6300 | 8000 |
| mean attenuation (dB) | 2.7 | 3.2 | 1.2 | 6.7 | 14.9 | 19.2 | 16.7 | 14.8 | 11.0 |
| Standard deviation (dB) | 3.5 | 3.1 | 6.5 | 4.2 | 5.3 | 4.0 | 3.7 | 4.8 | 3.8 |

From this test data, the ear tip pieces were given a noise reduction rating of −5. The noise reduction rating was calculated per NIOSH, http://www2a.cdc.gov/hp-devices/useHP-DC.html. These results show that the disclosed ear tip pieces provide more attenuation of frequencies ranging from 2000 Hz to 6300 Hz than for the lower or higher frequencies. As discussed in the Background of the Invention, this range of frequencies encompasses those frequencies at which the ear naturally has a higher resonance and would, therefore, require the most attenuation to prevent damage. Hence, the disclosed ear tip pieces attenuate sound the most at the frequencies that most require attenuation, while providing less attenuation of sound at the other frequencies. This provides hearing protection in the frequencies most likely to cause hearing damage or loss while helping maintain the quality and clarity of sound by not overly attenuating those frequencies that do not cause a high natural ear resonance and are generally more difficult to hear.

Additionally, studies have shown that at frequencies above 5000 Hz inserting a traditional earplug into a wearer's ear canal causes loss of the ear's natural resonance and also causes an unbalanced attenuation of sound that is approximately 15 dB to 20 dB greater than for lower frequencies. Patricia A. Niquette, MA, *Uniform Attenuation Hearing Pro-* tection *Devices*, Hearing Review, March 2007, http://www-.hearingreview.com/issues/articles/2007-03_07.asp. This results in a "treble deficiency" at frequencies above 5000 Hz, making sounds muffled and unclear. If a wearer has hearing loss in frequencies above 5000 Hz, wearing hearing protection that further muffles those high frequencies reduces the wearer's ability to communicate in a noisy environment. The disclosed ear tip pieces, as shown by the attenuation data discussed above, do not provide as much attenuation at frequencies above 5000 Hz, which enables a wearer to be able to hear sounds at those frequencies more clearly, thus, improving overall sound quality and clarity.

The disclosed ear tip piece's ability to selectively attenuate the most damaging frequencies is not provided by standard earplugs. For instance, Etymotic Research, Inc. located in Elk Grove Village, Ill. produces ETY—Plugs® and also provides information on those earplug's noise reduction rating on its website as form ER 20™. The noise reduction rating of these earplugs is 12. The attenuation data is shown below.

|  | Frequency in Hz | | | | | | |
| --- | --- | --- | --- | --- | --- | --- | --- |
|  | 125 | 250 | 500 | 1000 | 2000 | 4000 | 8000 |
| Mean Attenuation in dB | 13.2 | 15.3 | 16.7 | 18.3 | 20.8 | 18.3 | 21.6 |
| Standard Deviation in dB | 2.5 | 2.3 | 2.2 | 3.1 | 2.8 | 2.0 | 2.9 |

These results show that conventional earplugs provide an average attenuation at all frequencies, instead of the selective attenuation shown by the disclosed ear tip pieces. This results in the "insertion effect" discussed above at the lower frequencies, causing them to be more difficult to hear and diminishing the clarity and quality of sound.

Figure 17:
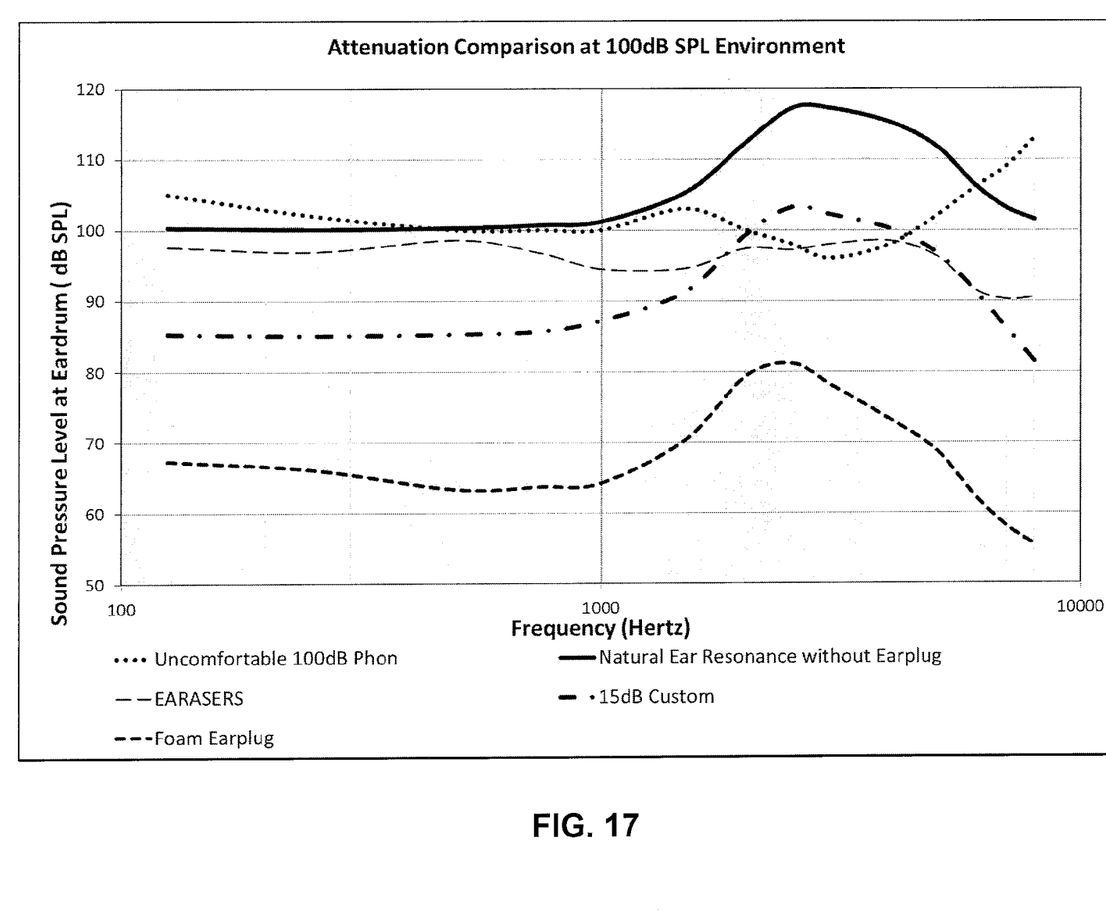
FIG. 17 is a line graph of the level of sound attenuation and frequency response of an embodiment of the present invention in comparison to a conventional earplug.

A comparison of the attenuation of the disclosed ear tip pieces, called Earasers, with conventional foam earplugs, 15 dB custom earplugs, an uncomfortable level of sound, and an ear's natural resonance without earplugs was graphed in the chart shown in FIG. 17 based on a 100 dB sound pressure level ("SPL") environment. The curves on the chart were determined by adding the natural ear resonance at a particular frequency with the earplug or ear tip piece's attenuation of sound at the same frequency. The "Uncomfortable 100 dB Phon" curve is generally known in the industry and is from Fletcher-Munson equal loudness contour curves, found in ISO 226:2006 revised. This curve represents 100 dB SPL at 1000 Hz and the corresponding equal loudness contour of other audible frequencies. The "Natural Ear Resonance without Earplug" curve is the result of adding the average adult ear rear ear unaided resonance ("REUR") from the National Acoustic Laboratories in Australia, which can be found in "Equations and Constants to Calculate NAL-NL1 Outputs", document version NAL-NL31, Feb. 9, 2006, p. 30, 45 d HS, to 100 dB SPL at all frequencies. The "EARASERS" curve is the result of adding the Natural Ear Resonance without Earplug to the above-mentioned Virginia Tech attenuation data obtained in accordance with ANSI Standard S3.19-1974. The "Foam Earplug" curve is the result of adding the Natural Ear Resonance without Earplug to attenuation data from Etymotic Research's ER20™ specification sheet for its ETY—Plugs®. The "15 dB Custom" curve is the result of adding the Natural Ear Resonance without Earplug to the attenuation data from Etymotic Research's ER15™ specification sheet for its custom earplugs.

The comparison chart shows that the disclosed ear tip piece, "EARASERS", produces a flat frequency response, unlike conventional foam earplugs or even custom earplugs. The disclosed ear tip piece's flat frequency response maintains the quality of sound while effectively protecting against hearing damage.

While various embodiments have been described, it will be apparent to those of ordinary skill in the art that many more embodiments and implementations are possible within the scope of the invention. Accordingly, the invention is not to be restricted except in light of the attached claims and their equivalents.

What is claimed is:

1. An ear tip piece for insertion in an ear canal to attenuate sound being transmitted to the ear, comprising:
    a first end including a solid portion that is sized and shaped to be inserted into and align the ear tip piece in the ear canal;
    a second end including a reversibly compressible portion formed by a hollow having flexible walls that adapt to the shape of the ear canal to create a seal;
    a channel formed in the solid portion that is open to the hollow for transmitting sound to the ear; and
    a sound attenuator positioned inside the channel for attenuating sound being transmitted to the ear.

2. The ear tip piece of claim 1, further comprising a bend between the first end and second end, the bend comprising an interior curve and an opposite curve that are sized and shaped to facilitate insertion of the ear tip piece at or near a first or second bend of the ear canal.

3. The ear tip piece of claim 1, further comprising a coupler inserted into the channel for retaining the sound attenuator.

4. The ear tip piece of claim 1, wherein the sound attenuator is a filter.

5. The ear tip piece of claim 1, wherein the sound attenuator is a plug.

6. The ear tip piece of claim 3, wherein a wax basket is fit inside the coupler for preventing the buildup of ear wax.

7. The ear tip piece of claim 3, wherein the coupler includes an extraction device to facilitate removal of the ear tip piece from the ear canal.

8. The ear tip piece of claim 3, wherein the coupler includes an insertion device to facilitate placement of the ear tip piece inside the ear canal.

9. The ear tip piece of claim 1, further comprising a cavity in the solid portion of the first end adjacent to the channel.

10. The ear tip piece of claim 2, wherein the bend forms an angle in a range from about 57° to about 87°.

11. The ear tip piece of claim 1, wherein the first and second ends are sized and shaped to be inserted in the ear canal such that no portion of the ear tip piece protrudes outside of the ear canal.

12. The ear tip piece of claim 2, wherein the interior curve has an angle of approximately 72°+/−15°.

13. The ear tip piece of claim 2, wherein the side of ear tip piece having the interior curve has a length of approximately 0.48 inches and the side of the ear tip piece having the opposite curve has a length of about 0.59 inches.

14. The ear tip piece of claim 2, wherein the side of ear tip piece having the interior curve has a length of approximately 0.49 inches and the side of the ear tip piece having the opposite curve has a length of about 0.60 inches.

15. An ear tip piece for insertion in an ear canal to attenuate sound being transmitted to the ear, comprising:
    a first end including a solid portion that is sized and shaped to be inserted into and align the ear tip piece in the ear canal;

a second end including a reversibly compressible portion formed by a hollow having flexible walls that adapt to the shape of the ear canal to create a seal;

a bend between the first end and second end, the bend comprising an interior curve and an opposite curve that are sized and shaped to facilitate insertion of the ear tip piece at or near a second bend of the ear canal;

a channel formed in the solid portion that is open to the hollow for transmitting sound to the ear; and a sound attenuator positioned in the channel to attenuate sound transmitted to the ear; and a coupler inserted into the channel for retaining the sound attenuator in the ear tip piece.

16. The ear tip piece of claim 1, wherein the sound attenuator is a damper.

17. The ear tip piece of claim 1, further comprising an extraction device.

18. The ear tip piece of claim 1, further comprising an insertion device.

19. The ear tip piece of claim 1, wherein the sound attenuator is replaceable.

20. The ear tip piece of claim 1, wherein the sound attenuator is positioned inside the channel close to the first end.

21. The ear tip piece of claim 15, wherein the interior curve has an angle of approximately 72°+/−15°.

22. An ear tip piece for insertion in an ear canal to attenuate sound being transmitted to the ear, comprising:

a first end including a solid portion that is sized and shaped to be inserted into and align the ear tip piece in the ear canal;

a second end including a reversibly compressible portion formed by a hollow having flexible walls that adapt to the shape of the ear canal to create a seal;

a bend between the first end and second end, the bend comprising an interior curve and an opposite curve that are sized and shaped to facilitate insertion of the ear tip piece at or near a first or second bend of the ear canal;

a channel formed in the solid portion that is open to the hollow for transmitting sound to the ear; and a sound attenuator positioned in the channel to attenuate sound transmitted to the ear, wherein the sound attenuator is positioned proximal to the ear drum when the ear tip piece is inserted in the ear canal.

* * * * *